United States Patent [19]

Dybas et al.

[11] 4,070,400
[45] Jan. 24, 1978

[54] DIPHENYL POLYAMIDES HAVING A CYCLOHEXYLENE MOIETY

[75] Inventors: Richard A. Dybas, Center Square, Pa.; Nathaniel Grier, Englewood; Bruce E. Witzel, Westfield, both of N.J.

[73] Assignee: Merck & Co., Inc., Rahway, N.J.

[21] Appl. No.: 622,935

[22] Filed: Oct. 16, 1975

[51] Int. Cl.² .............................................. C07C 87/38
[52] U.S. Cl. ........................ 260/570.5 P; 260/295.55; 260/343.7; 260/464; 260/501.18; 260/501.19; 260/501.2; 260/566 F; 260/570 R; 260/590 D; 260/570.5 CA; 252/107; 71/67; 424/54; 424/266; 424/280; 424/316; 424/330
[58] Field of Search ......... 260/570 R, 570.5, 570.5 D, 260/501.1, 343.7, 121; 424/316, 330

[56] References Cited

U.S. PATENT DOCUMENTS

| 3,197,510 | 7/1965 | Cyba | 260/584 |
|---|---|---|---|
| 3,751,471 | 8/1973 | Becker | 260/570.5 |
| 3,839,451 | 10/1974 | Hunt | 260/570.5 X |
| 3,872,171 | 3/1975 | Cronin et al. | 260/570.5 X |
| 3,876,702 | 4/1975 | Petersen et al. | 260/570.5 X |
| 3,900,565 | 8/1975 | Grisao et al. | 424/274 |

OTHER PUBLICATIONS

Derwant Abstracts, Japanese Pat. No. 50101-370.
Derwant Abstracts, Belg. Pat. No. 810,291.

*Primary Examiner*—Robert V. Hines
*Attorney, Agent, or Firm*—Edmunde D. Riedl; Julian S. Levitt

[57] ABSTRACT

Novel diphenyl and loweralkyl substituted diphenyl polyamines are useful antimicrobial agents, as well as algae inhibitors. They are especially useful because of their low toxicity, and as such are advantaeously included as the active agent in surgical scrubs, antibacterial soaps, as preservatives in cosmetic preparations, and the like. They also can be used for topical treatment of dermatological conditions having a bacterial origin or implication such as *Acne vulgaris*.

14 Claims, No Drawings

DIPHENYL POLYAMINES HAVING A CYCLOHEXYLENE MOIETY

DISCLOSURE OF THE INVENTION

This invention relates to a new class of polyamines which are useful as broad spectrum antimicrobial agents, as well as algae inhibitors. They are especially useful because of a surprisingly low toxicity and are particularly suitable for topical use including use in dermatological and cosmetic preparations, as well as surgical scrubs and hard surface disinfectants. These novel compounds have the structural formula:

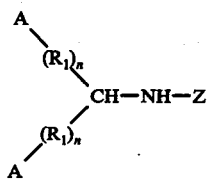

where each A is alike or different and is

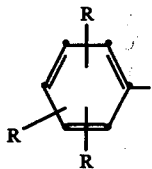

Each R is alike or different and is hydrogen or lower-alkyl;
Each n is alike or different and is the integer 0 or 1;
Each $R_1$ is alike or different and is $C_1$ to $C_4$ alkylene; and Z is

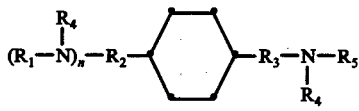

where
$R_2$ is 2-hydroxy-1,3-trimethylene, or $R_1$ as previously defined;
$R_3$ is 2-hydroxy-1,3-trimethylene, or $R_1$ as previously defined;
$R_4$ is hydrogen, aminoethyl, aminopropyl, $C_1$ to $C_4$ hydroxyalkyl, aminohydroxy $C_2$ to $C_4$ alkyl, or $C_2$ to $C_4$ dihydroxyalkyl;
$R_5$ is hydrogen, $C_1$ to $C_4$ hydroxyalkyl or $C_2$ to $C_4$ dihydroxyalkyl, aminohydroxy $C_2$ to $C_4$ alkyl, and n is as previously defined.

The compounds of this invention are preferably prepared according to the following sequence of reactions:

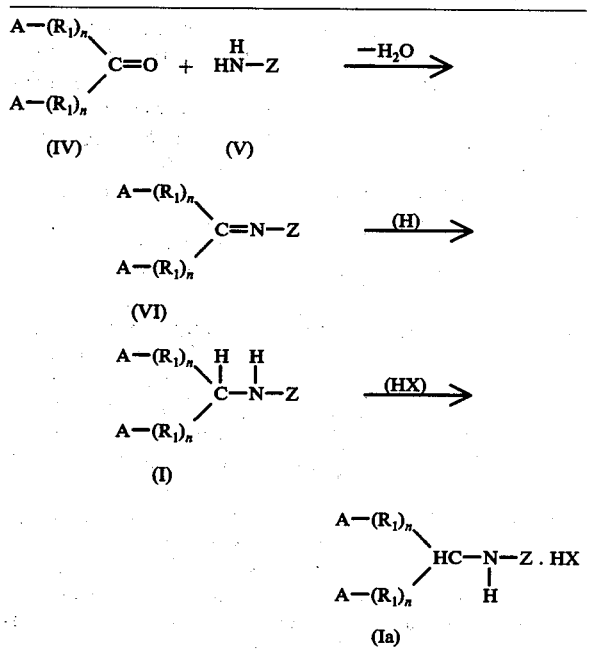

where A, Z and n have their previously defined meanings, HX is a mono or polybasic organic or inorganic acid, where sufficient HX is provided to protonate at least one amino group of phenyl polyamine compound I, to form salt I(a).

The preparation of phenyl polyamine I comprises the Schiff base reaction of the appropriate ketone IV and the appropriate amine V.

If amine V has two primary amino groups, it can either be symmetrical or unsymmetrical. An amine V, which is a symmetrical amine, e.g., where $R_2$ and $R_3$ are alike, n is 0, and $R_4$ and $R_5$ are hydrogen, forms a single Schiff base VI. This is because regardless of which terminal primary amine group of amine V reacts with ketone IV, the same product results. However, where amine V is unsymmetrical at least two products can result. For example, if $R_4$ is either aminoethyl or aminopropyl, there is obtained Schiff base VI

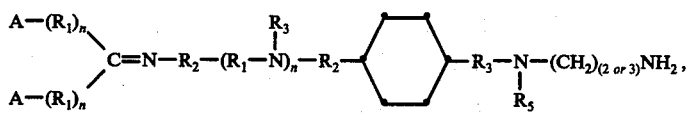

as well as Schiff base VI(a)

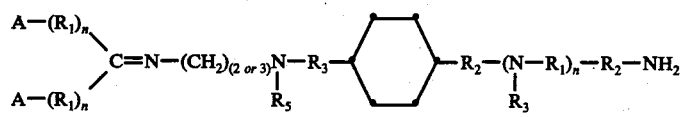

where A, $R_{1-6}$ and n are as previously defined. Note that both products VI and VI (a) come within the scope of the definition given for Schiff base VI. Where multiple products such as Schiff bases of formulas VI and VI(a) are produced, they can be separated, if desired, by the usual and well known separation techniques, i.e., distillation and the like.

As an alternative to obtaining a mixture of Schiff bases VI and VI(a) or VI(b), which upon reduction give a mixture of product I the reaction can be conducted stepwise. For example 1,4-bis-(2-aminoethyl)cyclohexstepane may be converted to a Schiff base with 1,5-di-(4-isopropyl)-phenyl)-3-pentanone, catalytically reduced, then the resulting amine selectively cyanoethylated with acrylonitrile, followed by catalytic hydrogenation to furnish N-(3-aminopropyl)-N'-[1,5-di-4-isopropylphenyl)-3-pentyl]-1,4-bis(2-aminoethyl) cyclohexane. A bis(primary amine) can be dicyanoethylated with excess acrylonitrile, catalytically reduced to the corresponding N,N'-bis-(3-aminopropyl) derivative and then converted by condensation with a ketone and reduction to the desired product. For example, dicyanoethylation of 1,4-bis-(2-aminoethyl) cyclohexane followed by catalytic reduction provides N,N'-bis-(3-aminopropyl)1,4-bis-(2-aminoethyl)cyclohexane. Condensation with 1-(2,4-dimethylphenyl)-6-(3-isopropylphenyl)-3-hexanone and subsequent catalytic hydrogenation of the -C=N bond affords N-(3-aminopropyl)-N'-{3-[1-(2,4-dimethylphenyl)-6-(3-isopropylphenyl)-3-hexylamino]-propyl}-1,4-bis-(2-aminoethyl) cyclohexane.

To prepare Schiff base VI, ketone IV and amine V are dissolved in a suitable inert solvent, for example, toluene, and heated to reflux, until reaction is substantially complete. Usually 5 to 20 hours is sufficient for water removal by azeotropic distillation. The solvent is then removed under reduced pressure and the residue comprising the Schiff base VI is dissolved in an inert solvent preferably an alkanol, such as ethanol or isopropanol.

After dissolution, the Schiff base VI is catalytically or chemically reduced.

In catalytic reductions, hydrogen saturates an alkanol solution of Schiff base VI using agitation in the presence of the usual hydrogenation catalysts, such as transition metals and their reducible oxides. Especially effective catalysts are the nobel metals and their oxides. A particularly preferred catalyst is platinum oxide. Generally, the hydrogenation reaction is carried out in a manner well known in the art. Small particles, e.g., 100–300 mesh of catalyst are admixed with the Schiff base and excess amine in alcohol and placed in a closed system pressurized with from 3–5 atmospheres of hydrogen gas. After reaction is complete, the pressure is released and the catalyst separated from the reaction mixture by filtration. The filtrate containing the phenyl polyamine I, is then further purified by usual techniques. Preferably, whatever solvent may be present is removed under reduced pressure, the residue then dissolved in a water-immiscible solvent, washed with water, followed by a further washing with a saturated aqueous inorganic salt solution. After drying, the solvent is removed by evaporation under reduced pressure giving the phenylpolyamine I usually as an oil. The phenylpolyamine can then be redissolved in loweralkanols, mixtures of loweralkanols and water, diethylether, dioxane and then neutralized with an acid, e.g., hydrogen chloride, or neutralized directly with aqueous acids.

Acid addition salts I(a) are then isolated, if desired, by precipitation, evaporation or other usually employed techniques.

Suitable anions X for the salt I(a) include anions derived from inorganic acids as well as those of organic acids such for example as halide, i.e., chloride, bromide or iodide or sulfate, nitrate, bisulfate, phosphate, acetate, propionate, maleate, succinate, laurate, palmitate, oleate, stearate ascorbate, gluconate, citrate carbonate, bicarbonate, benzoate, salicylate, pamoate, phthalate, furoate, picolinate, dodecylbenzenesulfonate, laurylethersulfate, nicotinate and the like. Generally, any anion derived from an acid is suitable and satisfactory when the polyamine salt anion $X^-$, e.g., chloride is replaced with other anions, by well known anion exchange techniques.

Alternatively, a chemical rather than a catalytic reduction is employed to reduce Schiff base VI to product I.

In this chemically reductive procedure, the ketone IV is reacted with the appropriate amine as before, but the Schiff base VI dissolved in an alkanol or inert ether-type solvent is reacted with a chemical reductant such as sodium borohydride or lithium aluminum hydride, respectively.

Although as little as an equivalent of the chemical reductant can be used successfully, more satisfactory results are obtained if at least two molar excess of and preferably at least a 2.5 molar excess of the chemical reductant is employed. After any initial reaction has subsided, the reaction mixture may be heated at reflux for an hour or two, then cooled to room temperature, and afterwards concentrated under vacuum. The residue obtained is then further purified as by treatment with mineral acid or inorganic base as was described for polyamines I and the salt may thereafter be formed as previously described.

The diphenyl ketones IV are readily prepared two alternative methods, are set forth below.

A. The Condensation of Acids — This method involves the following reaction scheme:

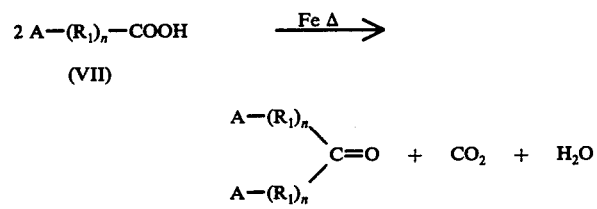

Acylative decarboxylation of acids VII is employed by heating the acid at elevated temperatures either with transition metals, preferably iron, transition metal oxides, alkaline earth oxides, with polyphosphoric acid or with boron trifluoride. Most suitably, acylative reaction is achieved by passage of acid vapors over catalysts such as heated thoria aerogel.

Condensation-decarboxylation of an acid is the preferred method for preparing ketone IV when each A-$(R_1)_n$ group is alike and n=1, a mixture of products being obtained when several different acids are combined in a reaction. The preferred reaction comprises admixing carboxylic acid VII with reduced iron powder and stirring in an inert atmosphere at 195° C. to 200° C. for 1–6 hours to form an iron salt.

Preferably, the carboxylic acid VII and iron are agitated under an inert atmosphere of nitrogen for at least 2 hours at 195° C. to 200° C.

After 2 hours, the temperature is increased suitably to 290° C. to 310° C. and agitation continued for at least another three hour period, four hours usually being sufficient. The reaction mixture is allowed to cool, and then is extracted with a suitable inert solvent such as diethylether and filtered. The solvent extracts are concentrated under reduced pressure. The residual liquid is distilled under vacuum to isolate the ketone IV.

The carboxylic acids VII employed above are prepared by various means well known in the art.

B. Condensation of Grignard and a Nitrile

Diphenyl alkanones can be obtained according to the following reaction scheme:

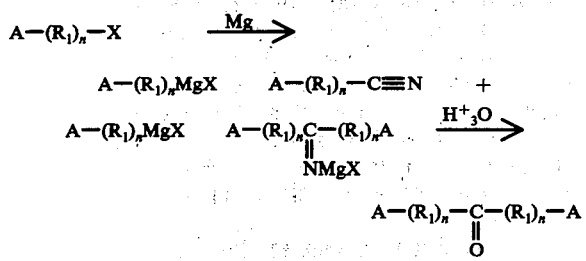

where A or $(R_1)_n$ of each reactant may be the same or different and are as previously defined.

This general procedure utilizes the reaction of a Grignard reagnet prepared from a chloro- or bromosubstituted phenyl derivative with a cyanosubstituted phenyl derivative. The resultant disubstituted iminoalkane Grignard complex is hydrolyzed with aqueous mineral acid to the corresponding ketone.

The Grignard reagent is obtained by reaction of the halide with magnesium metal, usually in the form of turnings or powder and may be catalyzed by very small concentrations of iodine or methyl iodide. Solvents which are useful include diethyl ether, dibutyl ether, tetrahydrofuran, dioxane and benzene. Usually, gentle warming suffices to initiate the reaction and the halide is gradually added to the metal-solvent mixture. After complete addition the disappearance of practically all magnesium metal signifies the end of the reaction. A small excess of halide is used and moisture must be excluded; a nitrogen atmosphere is beneficial. The Grignard reagent is then added to the nitrile, which is previously dissolved in two or three times its volume of solvent, over a period of 15 minutes to 1 hour at ambient temperature. The reaction mixture may then be heated to reflux to insure complete reaction. Generally, a small excess of Grignard reagent as compared to nitrile is employed. From 1 to 10 hours at reflux is sufficient for complete conversion. The resultant imine salt is preferably decomposed and hydrolyzed to the ketone with aqueous mineral acids such as hydrochloric, sulfuric and phosphoric. The ketones are water-insoluble and may be extracted with water-immiscible solvents. Purification is preferably accomplished by fractional distillation under reduced pressure. It is feasible to use the crude ketone reaction mixture for the alkylation of polyamines as the Grignard reaction by-products are usually alcohols of hydrocarbons and do not react with amines. The reactant halides, if present in the crude product, should be removed prior to the ketone-amine alkylation process.

The concentrations of Grignard reagent and nitrile may be varied over wide limits for securing good yields in the process. The halide and cyano, as well as carboxylic derivatives of phenyl compounds, e.g., phenylacetic acid are readily available.

Once the ketone IV is obtained it can then be reacted with a suitable polyamine V. Polyamines V which are exceptionally suitable for reaction with ketone IV include N,N'-bis-(3-amino-2-hydroxypropyl)-1,4-cyclohexanebis(methylamine); N-(3-aminopropyl)-1,4-cyclohexanebis(methylamine); N,N'-bis(3-aminopropyl)-1,4-bis(2-aminoethyl)-cyclohexane; N-(2-aminoethyl)-1,4-bis-(2-aminoethyl)cyclohexane; N-(2-hydroxyethyl)-1,4-cyclohexanebis(methylamine); N,N-bis-(3-hydroxypropyl)-1,4-cyclohexanebis(methylamine); N-(2,3-dihydroxypropyl)-1,4-cyclohexanebis(methylamine), and N-(3-aminopropyl)-N'-(2-hydroxyethyl)-1,4-cyclohexanebis(methylamine).

The compounds described herein are excellent broad spectrum antimicrobial agents which are especially effective against gram positive and negative bacteria, particularly troublesome gram-negative members of the genus Pseudomonas at aqueous concentrations of 1.0 to 100 ppm. Examples of susceptible species include, *inter alia, Staphylococcus aureus, Streptococcus pyogenes, Bordetella bronchiseptica, Corynebacterium acnes, Pasteurella multocida, Escherichia coli, Salmonella typhimurium, S. pullorum, Klebsiella pneumoniae, Aerobacter aerogenes, Pseudomonas aeruginosa, Desulfovibrio desulfuricans, Bacillus mycoides*, fungi such as *Aspergillus niger* and *Chaetomium globosum* and yeast such as *Candida albicans*, as well as algae.

For use, these compounds can be applied neat or employed in a diluted form. Satisfactory diluents include any inert material not destructive of the antimicrobial activity and especially liquid formulations comprising aqueous dispersions, solutions, and emulsions. Solid diluents include talc, corn starch, alumina and diatomaceous earth. The anitmicrobial agents of this invention can also be deposed on materials such as natural fibers including oaper, cotton, wool and synthetic fibers such as nylon, polypropylene, as well as upon inanimate surfaces including hard surfaces such as wood, glass, metal, tile, rubber, plastic, and porous surfaces such as concrete, leather and the like.

The polyamines of this invention are especially useful in suppressing the growth of aerobic and anaerobic bacteria in fluids employed in cutting and grinding operations, such as metal working, and oil well drilling muds or secondary oil recovery waters and brines. Anaerobes such as the sulfate-reducer, *Desulfovibrio desulfuricans*, are inhibited at 0.1-10 ppm. concentration of these polyamines. Suppression of these bacteria eliminates hydrogen sulfide production and corrosion of equipment, plugging of oil-bearing sands, malodors and other deleterious actions. These compounds are also useful in the preservation against biodeterioration of other aqueous systems such as aqueous emulsions and dispersions, paints or coatings, pigment suspensions, adhesives and the like where proliferation of microorganisms can produce colloid breakdown, pH shifts, malodors, corrosive substances, viscosity loss and other undesirable effects.

One particularly useful application of the compounds of this invention is imparting sanitizing properties to fabrics, either woven or non-woven, launderable or disposable, which are to be employed, such for example, as diapers, surgical masks, caps, gowns, towels and drapes, covers for hospital furniture or instrument wrappings, aseptic facial tissues and sanitary napkins and bathroom tissue. In this application, the compounds of Formula I can be applied to the fibrous pulp before extracting or strand or thread formation or it can be sprayed upon the finished goods. Either deposition technique is satisfactory so long as from $1 \times 10^{-4}\%$ or more by weight of the antimicrobial material is retained on the cloth. Greater than 0.1% to 1% by weight is generally excessive and superfluous.

Another application is alone or in solution or suspension or in conjunction with soaps or detergents for use in cleansing the skin, particularly in presurgical scrubbing formulations, or in formulations for controlling the growth of *Corynebacterium acnes*. *C. Acnes* is a strain of bacteria implicated in acne conditions, especially *Acne vulgaris*. Applications of as little as 1 to 5 ppm. is effective in controlling such skin dwelling bacteria. Larger concentrations can be used if desired without irritation or discomfort such as 2500 ppm and higher. Where the cleansing formulation is diluted with water upon use, the formulation can comprise from 0.01% by weight and more of the polyamine of this invention.

In addition, the compounds described herein can be employed in impounded water, such as swimming pools, ponds or industrially-used water such as cooling or papermill water to inhibit growth of undesirable bacteria, fungi, and/or algae.

In the control of slime-producing microorganisms and algae in recirculating industrial waters, particularly cooling operations and especially installations such as cooling towers, the polyamine compounds of this invention are usually employed alone, but can also be used in combination with other antimicrobial agents. The compounds are preferably employed as salts to enhance solubility. Concentrations in the recirculating water of as little as $1 \times 10^{-4}$% by weight are effective in inhibiting microbial growth. To insure effectiveness, especially against more resistant strains of microorganisms, and also when make-up water is added to replace water lost by evaporation and the like, concentrations of from $1 \times 10^{-4}$% to $5 \times 10^{-2}$% by weight are most satisfactory. Dosage may be continuous or as intermittent "shock treatment", i.e., addition in a 10–20 minute period every 4–8 hours.

An unusual, highly advantageous property of these compounds is high substantivity to all kinds of surfaces; this provides protection against corrosion and acts as a storage depot for continuously dosing the waters in contact. The same properties also are largely responsible for the previously stated utility as disinfectants for inanimate surfaces comprising walls and ceilings, equipment, animal pens, hospital facilities, kitchens and bathrooms and the like, and can be conveniently applied as a spray or an aerosol.

In formulating the compounds of this invention for the above uses, these compounds can be employed in combination with other antimicrobial agents, surfactants, insecticides, defoamers, odorants, or as chelates of metals such as copper, calcium, magnesium and iron.

Agricultural uses for these compounds include the control of microbial damage to plants and seeds by application to the involved surfaces areas. The compounds of this invention show high orders of bacterial inhibition and are especially useful for this purpose. Some of the diseases which are of commercial importance in decreasing yield and quality and are controlled by the compositions of the invention are fire blight of apple and pear, bacterial spot on stone fruit, cherry leaf spot, walnut blight, common blight of bean, bacterial spot of tomato and pepper, and potato seed piece decay. The effective concentration of polyamines required varies from 5–100 parts per million; they may be applied as dusts, powder dispersions, aqueous solutions, emulsions in water, or as aqueous dipping baths. Other plant diseases which can be controlled by treatment with these formulations are fungal in origin, such as the many kinds of powdery mildew and leaf scabs.

For seed treatment, proportions as low as 1 to 4 ounces per hundred weight (550 to 660 ppm on seed) are effective against various fungi.

For agricultural uses, the compounds of the invention are most suitably used in the form of aqueous suspensions or emulsions, the free base products being generally insoluble in water. For this type of formulation various powdered carriers can be employed to aid in achieving uniform distribution. Talc, fuller's earth, calcium silicate, calcium carbonate, clays and the like are admixed with the agent along with wetting and dispersing agents and sticking agents. For maximum chemical compatability those which are non-ionic in character are preferred. Other anionic or cationic surfactants are also satisfactory.

Additional applications for the compounds of this invention include inhibiting formation of dental plaque especially when used as an oral rinse, e.g., a mouth wash, or in combination with a toothpaste or tooth powder containing from 50–1,000 ppm.

The following specific examples are further illustrative of our invention, but should not be construed as any limitation on the compound presented in formula I or the appended claims.

PREPARATION A

Preparation of 1,5-Di-(4-Isopropylphenyl)-3-pentanone 3-(4-Isopropylphenyl)propionic acid (0.20 mole) and iron (hydrogen reduced, 6.15 g., 0.11 mole) are heated for 1.5 hours at 195° C. under a nitrogen atmosphere. After that time, the temperature is increased to 290° C. and maintained at that temperature for three hours. The cooled reaction mass is extracted well with ether, filtered through Celite, and the etheral extracts concentrated under vacuum. The residue is stripped under vacuum to leave the product, 17.3 g. (51%).

In an analogous manner there are obtained the following ketones.
1,7-Di-(4-isopropylphenyl)-4-heptanone;
1,9-Diphenyl-5-nonanone;
1,5-Diphenyl-3-pentanone;
1,3-Diphenylacetone;
1,3-Di-(4-isopropylphenyl) acetone;
1,7-Diphenyl-4-heptanone;
1,3-Di-(4-t-butylphenyl) acetone;
1,7-Di-(4-ethylphenyl)-4-heptanone;
1,7-Di-(2-methyl-5-t-butylphenyl)-4-heptanone;
1,5-Di-(2-isopropylphenyl)-3-pentanone;
1,5-Di-(2,4,6-trimethylphenyl)-3-pentanone;
1,9-Di-(2-ethylphenyl)-5-nonanone;
1,5-Di-(4-t-bitylphenyl)-3-pentanone;
1,5-Di-(4-methylphenyl)-3-pentanone;
1,7-Di-(4-t-butylphenyl)-4-heptanone.

PREPARATION B

Preparation of 4-Phenyl-1-(4-isopropylphenyl)-butanone-2

A Grignard reagent was prepared from 2-phenylethyl bromide 21 gm. (0.11 mole) and magnesium, 2.4 g. (0.1 gram atom). The magnesium is covered with 25 ml. of anhydrous ether, a crystal of iodine added and in a nitrogen atmosphere, the halide dissolved in 50 ml. of anhydrous ether is added, once initial reaction is obtained, at reflux temperature over a period of 1-2 hours. After complete addition, refluxing is continued for ½ hour.

In a nitrogen atmosphere, the Grignard solution is clarified by passage through a glass wool filter plug and added slowly to an agitated solution of 4-isopropylphenylacetonitrile, 14.9 gm. (0.09 mole) in 200 ml. of anhydrous diethyl ether. A gentle reflux is maintained during the addition which requires ½ to 1 hour. After complete addition and an additional 15 minutes at reflux, the reaction mixture is cooled and poured onto a mixture of 50 ml. of concentrated hydrochloric acid and 200 gms. of ice using good mixing. Upon warming the ether is removed by distillation and the residue heated at 70°-100° C. for 1 hour. The product is extracted with two portions, 250 ml. each of ether, the ether solution dried over anhydrous magnesium sulfate and the solvent removed. Any of the reactants, i.e., halide and nitrile, are separated from the ketone by fractional distillation under reduced pressure along with by-products.

In a similar procedure, the following ketones are prepared:
1-(2-Methylphenyl)-4-phenylpentan-2-one;
1-(4-t-Butylphenyl)-5-(4-isopropylphenyl)-pentan-3-one;
2-(3-Methylphenyl)-8-(2-isopropylphenyl)-octan-4-one;
1-(3-Methylphenyl)-4-(4-n-butylphenyl)-2-pentanone;
1,4-Di-(4-isopropylphenyl)-2-butanone;
1-Phenyl-3-(4-t-butylphenyl)acetone;
1-(3,4-Dimethylphenyl)-5-(4-isopropylphenyl)-3-pentaonone;
2,6-Diphenyl-4-heptanone.

PREPARATION C

Preparation of N-(3-Aminopropyl)-1,4-cyclohexanebis-(methylamine)

Acylonitrile (26.5 g., 0.5 mole) is added dropwise over a 45 minute period to 1,4-cyclohexanebis(methylamine) (2.84 g., 2.0 mole) with stirring and ice bath cooling. After complete addition, the reaction mixture is stirred an additional 1 hour at 5° C., gradually warmed to 45° C. and kept 2 hours at that temperature followed by 1 hour at 90° C. The reaction mixture is stripped of any unreacted acylonitrile and excess non-cyanoethylated bis(methylamine) starting material which was removed at an internal temperature of 110° C. and 1 mm. The residue is then dissolved in 1.5 l. of ethyl alcohol (ammonia gas saturated) mixed with 50 ml. of sponge nickel catalyst and hydrogenated at 150 psi. After removal of catalyst by filtration, the solvent and ammonia is stripped off and the triamine product purified by fractionation under reduced pressure.

A higher homolog, N-(3-aminopropyl)-1,4-cyclohexanebis-(2-ethylamine) is synthesized using the above procedure with 1,4-bis-(2-aminoethyl)cyclohexane prepared according to P. P. Garcia and J. H. Wood, *J. Org. Chem.*, 26, 4167 (1961). Excess staring amine in this example may be separated from product at a boiling point of 122° C.-126° C./1 mm.

PREPARATION D

Preparation of N-(3-Aminopropyl)-N'-(2-hydroxyethyl)-1,4-cyclohexanebis(methylamine)

Acylonitrile (10.6 g., 0.2 mole) is added dropwise over a 15 minute period to N-(2-hydroxyethyl)-1,4-cyclohexanebis(methylamine) (37.2 g., 0.4 mole) with stirring and ice bath cooling. After complete addition, the reaction mixture is stirred an additional 2 hours at 5° C., allowed to gradually warm over a 1 hour period, heated 2 hours at 45° C. It is then fractionated under reduced pressure up to an internal temperature of 170° C. The residue is dissolved in 200 ml. ethyl alcohol, cooled in an ice bath and saturated with ammonia gas at 0° C. Approximately 5 ml. of sponge nickel catalyst (W. R. Grace Co., Davison Chem. Division) is added and the mixture shaken under hydrogen at 150 psi until no further hydrogen uptake. The catalyst is removed by suction, filtration under nitrogen, the solvent stripped away and the residue fractionally distilled under reduced pressure. The triamine product is readily distinguished from cyanoethylated diamine by its lower $R_f$ on slica gel using a solution of 1 volume concentrated aqueous ammonium hydroxide in 4 volume methyl alcohol. The synthesis is an adaptation of the method of M. Israel et al, *J. Med. Chem.*, 7, 710 (1964) for the preparation of polymethylenepolyamines.

PREPARATION E

Preparation of N-(2-Hydroxyethyl)-1,4-cyclohexanebis(methylamine)

A solution of 14.2 gm. (0.1 mole) of 1,4-cyclohexanebis(methylamine) in 150 ml. anhydrous methyl alcohol and under an atmosphere of nitrogen is warmed to 45° C.-50° C. In a 20 minute period, there is introduced with good agitation and beneath the liquid surface a total of 1.1 gm. (0.025 mole) of ethylene oxide in gaseous form. The reaction temperature is maintained at 45° C.-50° C. for an additional one-half hour after stopping the addition of ethylene oxide. The methyl alcohol is removed by distillation at atmospheric pressure; excess 1,4-cyclohexanebis(methylamine) is readily separated from the product by fractionation under reduced pressure. Only monoethoxylated compound remained and could be used as such or further purified by distillation at reduced pressure.

PREPARATION F

Preparation of N-(3-Amino-2-hydroxypropyl)-1,4-cyclohexanebis(methylamine)

1,4-Cyclohexanebis(methylamine) (14.2 g., 0.1 mole) is dissolved in 50 ml. of anhydrous methyl alcohol and the solution cooled to +5° C. in an ice bath. Epichlorohydrin (9.3 g., 0.1 mole) is added in a 2-minute period and the temperature maintained at +5° C. for 2 hours; reaction is allowed to continue at 10° C-15° C. until thin layer chromatography of an aliquot (silica gel plate with development using a solution of 1 volume concentrated aqueous ammonium hydroxide in 4 volumes of methyl alcohol) indicated nearly complete conversion of the starting diamine to the propylene chlorohydrin. The solution is then added to 100 ml. of dry with methyl alcohol previously saturated at 0° C. with dry ammonia gas by continuous dropwise flow at +5° C. with good agitation and external cooling. After stirring 2 hours at °5° C., it is allowed to warm to 20° C. and mixed overnight. The reaction is competed by heating at 45° C.-55° C. for 6 hours. The solvent and ammonia was removed by stripping and the product purified using fractional distillation under reduced pressure.

N-(2,3-Dihydroxypropyl)-1,4-cyclohexanebis(methylamine) is produced by alkaline hydrolysis of the above propylenechlorohydrin derivative.

The propylene chlorohydrin derivative is dissolved in a 1M sodium hydroxide solution containing 50% methyl alcohol and 50% water by weight in a ratio of 5 grams of chlorohydrin to 25 ml. of sodium hydroxide solution. After stirring 24 hours at 20° C. the methyl alcohol is removed by distillation and the oil which separates is extracted with 100 ml. of diethyl ehter. The extract is washed with approximately 10 ml. of cold water, the ether layer dried over anhydrous sodium sulphate and then filtered. Removal of the ether by distillation leaves the product in good purity as an oil.

PREPARATION G

Preparation of N,N'-bis-(3-Aminopropyl)-1,4-bis-(2-aminoethyl)cyclohexane

Acrylonitrile (10.6 g., 0.2 mole) is added dropwise over a 15 minute period to 1,4-bis-(2-aminoethyl)-cyclohexane (17.0 g., 0.1 mole) cooled in an ice bath and with good stirring. The resultant solution is maintained at 5° C. –10° C. with agitation for 1 hour, allowed to warm to 25° C. over a 2 hour period and finally heated at 90° C.–95° C. for 4 hours. The reaction mixture is then freed of any unreacted material and monocyanoethylated product by gradually heating to an internal temperature of 130° C. at a pressure of 0.5–1 mm. The residue is dissolved in 200 ml. ethyl alcohol which had been previously saturated with dry ammonia gas at 0° C., mixed with approximately 5 ml. of a sponge nickel catalyst suspension and reduced with shaking under 200 psi hydrogen. The catalyst is removed by suction filtration, the filtrate stripped of solvent and the residue purified by fractional distillation under reduced pressure.

PREPARATION H

Preparation of N-(2-Aminoethyl)-1,4-bis-(2-aminoethyl)-cyclohexane 1,4-Bis(2-aminoethyl) cyclohexane (68 g,m., 0.4 mole) and ethyleneimine (4.3 gm., 0.1 mole) with 0.4 g. ammonium chloride are mixed in a glasslined pressure reactor and filled with nitrogen to 100 psi. The mixture is shaken and heated at 85° C.–95° C. for 48 hours. After cooling, it is distilled rapidly free of the salt and then fractionated under high vacuum. The starting diamine is readily distinguished from the triamine product by thin layer chromatography and silica gel using a mixture of 1 volume concentrated aqueous ammonium hydroxide with 4 volume methyl alcohol, the diamine having a much higher $R_f$.

PREPARATION I

N,N-Bis-(3-hydroxypropyl)-1,4-cyclohexanebis(methylamine)

Preparation of 1-Cyano-4-[di-(3-hydroxypropyl)aminomethyl]-cyclohexane and catalytic reduction a. 1-Bromomethyl-4-cyanocyclohexane (20.2 g., 0.1 mole) and di-(3-hydroxypropyl)amine (53.2 g., 0.4 mole) in 400 ml. of anhydrous isopropyl alcohol are heated in an autoclave at 105° C.–115° C. for 8 hours with continuous agitation. The reaction mixture is stripped of solvent under reduced pressure and the residue diluted with 500 ml. of ice water. A cold solution of 5 g. of sodium hydroxide in 100 ml. of water is added and the mixture extracted with two 150 ml. portions of methylene chloride. The organic phase is then washed with 50 ml. of ice water, dried overnight with anhydrous sodium sulfate, filtered and freed of solvent by distillation under reduced pressure.

b. The residual oil from a.) is taken up in 200 ml. of anhydrous ethyl alcohol previously saturated at 0° C. with dry ammonia gas, mixed with 5 ml. of sponge nickel catalyst suspension and hydrogenated at 25° C. under 100 psi hydrogen pressure in a stirred autoclave. The reaction completion is readily determined by disappearance of the C≡N IR absorption band and measurement of hydrogen uptake. The catalyst is removed by suction filtration, the solvent with mild heating under reduced pressure and the product obtained pure with fractional distillation at reduced pressure.

EXAMPLE 1

N,N'-bis-(3-aminopropyl)-1,4-bis-(2-aminoethyl)-cyclohexane and 1,5-di(4-isopropylphenyl)-3-pentanone in 250 ml. toluene is heated at reflux overnight with a Dean-Stark water separator. The cooled solution is concentrated under reduced pressure. The residue is dissolved in ethanol and hydrogenated with 1.5 g. PtO₂ at room temperature and 40 psi hydrogen pressure. The platinum catalyst is filtered off and the ethanol removed under vacuum. The residual oil is dissolved in ether and the ether solution washed several times with water to remove the excess 3,3'-iminobispropylamine. The ether extracts are dried over anhydrous sodium sulfate and concentrated under vacuum to leave the polyamine as a colorless oil.

The o8il is dissolved in ether and hydrogen chloride gas is bubbled into the solution until no further precipitation occurs. The ether is evaporated under reduced pressure to leave the product as a solid which is digested with hot isopropyl alcohol. The solids are collected by filtration and dried under vacuum at 70° C. to give a colorless product, N-(3-aminopropyl)-N'-[3-[1,5-di-(4-isopropylphenyl)-3-pentylamino]propyl]-1,4-bis-(2-aminoethyl) cyclohexanetetrahydrochloride.

In an analogous manner from the ketones and the amines set forth below, there are prepared the following compounds of this invention.

TABLE I

| Ketone | Amine | Product |
| --- | --- | --- |
| 1,7-Di-(4-t-butylphenyl)-4-heptanone | N,N'-bis-(3-aminopropyl)-1,4-bis-(2-aminoethyl)cyclohexane | N-(3-aminopropyl)-N'-{3-[1,7-di-(4-t-butylphenyl)-4-heptylamino]propyl}-1,4-bis-(2-aminoethyl)cyclohexane |
| 1,7-Di-(2-methyl-5-t-butylphenyl)-4-heptanone | N,N'-bis-(3-aminopropyl)-(2-aminoethyl) cyclohexane | N-(3-aminopropyl)-N'-{3-[1,7-di-(2-methyl-5-t-butylphenyl)-4-heptylamino]propyl}-1,4-bis-(2-aminoethyl) cyclohexane |
| 1,5-Di-(4-methylphenyl)- | N,N'-bis-(3-aminopropyl)- | N-(3-aminopropyl)-N'-{3-[1,5-di-(4-methyl- |

TABLE I-continued

| Ketone | Amine | Product |
| --- | --- | --- |
| 3-pentanone | 1,4-bis-(2-aminoethyl)-cyclohexane | phenyl)-3-pentylamino]propyl}-1,4-bis-(2-aminoethyl) cyclohexane |
| 1,5-Di-(2,4,6-trimethylphenyl)-3-pentanone | N-(2,3-dihydroxypropyl)-1,4-cyclohexanebis-(methylamine) | N-(2,3-dihydroxypropyl)-N'-[1,5-di-(2,4,6-trimethylphenyl)-3-pentyl]-1,4-cyclohexanebis-(methylamine) |
| 1,7-Di-(4-isopropylphenyl)-4-heptanone | N-(2,3-dihydroxypropyl)-1,4-cyclohexanebis-(methylamine) | N-(2,3-dihydroxypropyl)-N'-]1,7-di-(4-isopropylphenyl)-4-heptyl]-1,4-cyclohexanebis-(methylamine) |
| 1,3-Di-(4-t-butylphenyl)-acetone | N-(3-aminopropyl)-N'-2-hydroxyethyl-1,4-cyclohexanebis(methylamine) | N-{3-[1,3-di-(4-t-butylphenyl)-2-propylamino]-propyl}-N'-(2-hydroxyethyl)-1,4-cyclohexane-bis(methylamine) |
| 1,5-Di-(4-isopropylphenyl)-3-pentanone | N-(3-aminopropyl)-N'-2-hydroxyethyl-1,4-cyclohexanebis(methylamine) | N-(2-hydroxyethyl)-N'-{3-[1,5-di-(4-isopropylphenyl)-3-pentylamino]propyl}-1,4-cyclohexanebis(methylamine) |
| 1,3-Di-(4-isopropylphenyl)-acetone | N-(3-aminopropyl)-N'-2-hydroxyethyl-1,4-cyclohexanebis(methylamine) | N-(2-hydroxyethyl)-N'-{3-[1,3-di-(4-isopropylphenyl)-2-propylamino]propyl}-1,4-cyclohexanebis(methylamine) |
| 1,3-Di-(4-t-butylphenyl)-acetone | N-(2,3-dihydroxypropyl)-1,4-cyclohexanebis-(methylamine) | N-[1,3-di-(4-t-butylphenyl(-2-propyl]-N'-(2,3-dihydroxypropyl)-1,4-cyclohexanebis-(methylamine) |
| 1,9-Diphenyl-5-nonanone-diphenyl | N-(2,3-dihydroxypropyl)-1,4-cyclohexanebis-(methylamine) | N-(2,3-dihydroxypropyl)-N'-(1,9-diphenyl-5-nonyl)-1,4-cyclohexanebis(methylamine) |
| 1,5-(Diphenyl-3-pentanone | N,N'-bis-(3-aminopropyl)-1,4-bis-(2-aminoethyl)-cyclohexane | N-(3-aminopropyl)-N'-[3-(1,5-diphenyl-3-pentylamino)propyl]-1,4-bis-(2-aminoethyl)cyclohexane |
| Dibenzylketone | N,N'-bis-(3-aminopropyl)-1,4-bis-(2-aminoethyl)-cyclohexane | N-[3-aminopropyl)-N'-[3-(1,3-diphenyl-2-propylamino)propyl]-1,4-bis-(2-aminoethyl)-cyclohexane |
| 1,7-Diphenyl-4-heptanone | N-(3-aminopropyl)-N'-2-hydroxyethyl-1,4-cyclohexanebis(methylamine) | N-[3-(1,7-diphenyl-4-heptylamino)propyl]-N'-(2-hydroxyethyl)-1,4-cyclohexanebis-(methylamine) |
| 1,7-Di-(4-ethylphenyl)-4-heptanone | N-(3-aminopropyl)-N'-2-hydroxyethyl-1,4-cyclohexanebis(methylamine) | N-{3-[1,7-di-(4-ethylphenyl)-4-heptyl-amino]propyl}-N'-(2-hydroxyethyl)-1,4-cyclohexanebis(methylamine) |
| 1,5-Di-(2-isopropylphenyl)-3-pentanone | N,N'-bis-N-(3-hydroxypropyl)-1,4-cyclohexanebis-(methylamine) | N-(3-hydroxypropyl)-N'-]1,5-di-(2-isopropylphenyl)-3-pentyl]-1,4-cyclohexane-bis(methylamine) |
| 1,9-Di-(2-ethylphenyl)-5-nonanone | N,N'-bis-N-(3-hydroxypropyl)-1,4-cyclohexanebis-(methylamine) | N-[1,9-di-(2-ethylphenyl)-5-nonyl]-N'-(3-hydroxypropyl)-1,4-cyclohexanebis-(methylamine) |
| 1-(3-Methylphenyl)-5-(4-n-butylphenyl)-4-pentanone | N-(3-aminopropyl)-N'-2-hydroxyethyl)-1,4-cyclohexanebis(methylamine) | N-(2-hydroxyethyl)-N'-{3-[1-(3-methylphenyl)-5-(4-n-butylphenyl)-4-pentylamino]-propyl}-1,4-cyclohexanebis(methylamine) |
| 1,4-Di-(4-isopropylphenyl)-2-butanone | N-(3-aminopropyl)-N' -2-hydroxyethyl)-1,4-cyclohexanebis(methylamine) | N-(2-hydroxyethyl)-N'-{3-[1,4-di-(4-isopropylphenyl)-2-butylamino]propyl}-1,4-cyclohexanebis(methylamine) |
| 1-Phenyl-3-(4-t-butylphenyl)acetone | N-(2,3-dihydroxypropyl)-1,4-cyclohexanebis-(methylamine) | N-(2,3-dihydroxypropyl)-N'-]1-phenyl-3-4-t-butylphenyl)-2-propyl]-1,4-cyclohexane-bis(methylamine) |
| 1-(3,4-Dimethylphenyl)-5-(4-isopropylphenyl)-3-pentanone | N-(2,3-dihydroxypropyl)-1,4-cyclohexanebis-(methylamine) | N-(2,3-dihydroxypropyl)-N'-[1-(3,4-dimethylphenyl)-5-(4-isopropylphenyl)-3-pentyl]-1,4-cyclohexanebis(methylamine) |
| 2,6-Diphenyl-4-heptanone | N-(2,3-dihydroxypropyl)-1,4-cyclohexanebis-(methylamine) | N-(2,3-dihydroxypropyl)-N'-(2,6-diphenyl-4-heptyl)-1,4-cyclohexanebis(methylamine) |
| 1,7-Di-(4-t-butylphenyl)-4-heptanone | N-(3-aminopropyl)-1,4-cyclohexanebis(methylamine) | N-3-aminopropyl-N'-[1,7-di-(4-t-butylphenyl)-4-heptyl]-1,4-cyclohexanebis-(methylamine) and N-[4-(aminomethyl)cyclohexylmethyl]-N'-[1,7-di-(4-t-butylphenyl)-4-heptyl]-1,3-diaminopropane |
| 1,5-Di-(4-isopropylphenyl)-3-pentanone | N-(2-aminoethyl)-1,4-bis-(2-aminoethyl)cyclohexane | N-(2-aminoethyl)-N'-[1,5-di-(4-isopropylphenyl)-3-pentyl]-1,4-bis-(2-aminoethyl)-cyclohexane and N-[2-(4- 2-aminoethyl cyclohexyl)ethyl]-N'-[1,5-di-(4-isopropylphenyl)-3-pentyl]-ethylenediamine |
| 1-(4-t-Butylphenyl)-6-(4-i-propylphenyl)-3-hexanone | N-(2-hydroxyethyl)-1,4-cyclohexanebis(methylamine) | N-(2-hydroxyethyl)-N'-[1-(4-t-butylphenyl)-6-(4-i-propylphenyl)-3-hexyl]-1,4-cyclohexanebis(methylamine) |
| 1,7-Di-(4-ethylphenyl)-4-heptanone | N,N'-bis-(3-hydroxypropyl)-1,4-cyclohexanebis- | N,N-bis-(3-hydroxypropyl)-N'-[1,7-di-(4-ethylphenyl)-4-heptyl]-1,4-cyclohexanebis-(methylamine) |
| 1-(4-i-propylphenyl)-3-(3,4,5-trimethylphenyl)-acetone | N-(2,3-dihydroxypropyl)-1,4-cyclohexanebis-(methylamine) | N-(2,3-dihydroxypropyl)-N'-[1-(4-i-propylphenyl)-3-(3,4,5-trimethylphenyl)-2-propyl]-1,4-cyclohexanebis(methylamine) |
| 1,7-Di-(5-t-butyl-2-methylphenyl)-4-heptanone | N-(3-aminopropyl)-N'-(2-hydroxyethyl)-1,4-cyclohexanebis(methylamine) | N-(3-aminopropyl)-N-(2-hydroxyethyl)-N'-[1,7-di-(5-t-butyl-2-methylphenyl)-4-heptyl]-1,4-cyclohexanebis(methylamine) and N-[4-(aminomethyl)cyclohexylmethyl]-N-(2-hydroxyethyl)-N'-[1,7-di-(5-t-butyl-2-methylphenyl)-4-heptyl]-1,3-diaminopropane |
| 1,5-Di-(4-isopropylphenyl)-3-pentanone | N-(3-aminopropyl)-1,4-cyclohexanebis(methylamine) | N-(3-aminopropyl)-N'-[1,5-di-(4-isopropylphenyl)-3-pentyl]-1,4-cyclohexanebis(methylamine) and N-[4-(aminomethyl)cyclohexylmethyl]-N-(3-aminopropyl)-N'-[1,5-di-(4-isopropylphenyl)-3-pentyl]-1,3-diaminopropane |

TABLE I-continued

| Ketone | Amine | Product |
|---|---|---|
| 1,7-Di-(5-t-butyl-2-methyl-phenyl)-4-heptanone | N,N'-bis-(3-aminopropyl)-1,4-cyclohexanebis-(methylamine) | N-(3-aminopropyl)-N'-[N-(1,7-di-(5-t-butyl-2-methylphenyl)-4-heptyl)-3-aminopropyl]-1,4-cyclohexanebis(methylamine) |
| 1,7-Di-(4-t-butylphenyl)-4-heptanone | N-(3-aminopropyl)-1,4-cyclohexanebis-(methylamine) | N-3-aminopropyl-N'-[1,7-di-(4-t-butylphenyl)-4-heptyl]-1,4-cyclohexanebis(methylamine) and N-[4-(aminoethyl)cyclohexylmethyl]-N'-[1,7-di-(4-t-butylphenyl)-4-heptyl]-1,3-diaminopropane |
| 1,7-Di-(4-ethylphenyl)-4-heptanone | N,N'-bis-(3-amino-2-hydroxypropyl)-1,4-cyclohexanebis-(methylamine) | N-(3-Amino-2-hydroxypropyl)-N'-{3-[1,7-di-(4-ethylphenyl)-4-heptylamino]-2-hydroxypropyl}-1,4-cyclohexanebis(methylamine) |
| 1-(4-i-propylphenyl)-3-(3,4,5-trimethylphenyl)-acetone | N,N'-bis-(3-aminopropyl)-1,4-bis-(2-aminoethyl)-cyclohexane | N-(3-aminopropyl)-N'-3-[1-(4-i-propylphenyl)-3-(3,4,5-trimethylphenyl)-2-propylamino]propyl-1,4-bis-(2-aminoethyl)cyclohexane |

EXAMPLE 2

Preparation of N-(2-hydroxyethyl)-N'-[1-(4-isopropylphenyl)-4-phenyl-2-butyl]cyclohexylene-1,4-bis-(2-ethylamine)dichloride. A mixture of 1-(4-isopropylphenyl)-4-phenylbutanone-2 (5.3 g., 0.02 mole) and N-(2-hydroxyethyl)cyclohexylene-1,4-bis-(2-ethylamine) (21.4 g., 0.1 mole) in 150 ml. of toluene is heated at reflux overnight with a Dean-Stark spearator. The toluene is then removed under vacuum. The residual oil dissolved in 25 ml. isopropanol is added dropwise to sodium borohydride (1.90g., 0.05 mole, excess) suspended in 50 ml. isopropanol. After complete addition, the reaction mixture is heated at reflux for one hour. The isopropanol is evaporated under reduced pressure, the residue treated with water and the aqueous mixture extracted well with ether. The combined ether extracts are back-washed with water, a saturated sodium chloride solution, dried over anhydrous sodium sulfate and concentrated under vacuum to leave the polyamine product.

This product is dissolved in ether and the solution cooled in an ice-water bath. Hydrogen chloride gas is bubbled into the solution until no further precipitate is formed. The solid is collected by filtration, washed with a small amount of ether, and dried under vacuum to leave the polyamine dihydrochloride as a colorless product.

EXAMPLE 3

Preparation of N-(3-aminopropyl)-N'-[1,7-di(2-methyl-5-t-butylphenyl)-4-heptyl]-1,4-bis-(2-aminoethyl)-cyclohexane. A mixture of 1,7-di-(2-methyl-5-t-butylphenyl)-4-heptanone (12.2 g., 0.03 mole) and 1,4-bis-(2-aminoethyl)cyclohexane (17 g., 0.1 mole) in 250 ml. ethanol is heated at reflux overnight under vacuum. The cooled reaction mixture is hydrogenated with $PtO_2$ at room temperature and 40 psi hydrogen pressure. The platinum catalyst is filtered off and the ethanol removed under reduced pressure. The residual oil is dissolved in ether and the ether solution washed several times with water to remove the excess diaminoethane.

The ether extracts are dried over anhydrous sodium sulfate and concentrated under vacuum to leave an oil.

The oil is dissolved in 20 ml. tert-butanol and chilled to 0° C.–5° C. in an ice-water bath. Acrylonitrile (1.75 g., 2.2 ml., 0.033 mole) is added dropwise over a 5-minute period. The reaction mixture is allowed to warm up to room temperature and is then heated at 60° C. overnight. The t-butanol was removed under reduced pressure. The residual oil was dissolved in 150 ml. glacial acetic acid and hydrogenated with $PtO_2$ at room temperature and 40 psi hydrogen pressure. The platinum catalyst is filtered off and the acetic acid removed under vacuum. The residue is dissolved in ether and made basic with 10% sodium hydroxide. The ether solution is washed with water, dried over anhydrous sodium sulfate and concentrated under reduced pressure.

In addition to the compounds specifically set forth in the foregoing examples, each of the respective ketones set forth in Preparations A and B when reacted with the individual amines set forth in the foregoing specification especially at pahges 10 and 11 according to the method set forth in Example I produce the entire range of compounds described according to this invention as embodied in Formula I.

What is claimed is:

1. A compound of the formula:

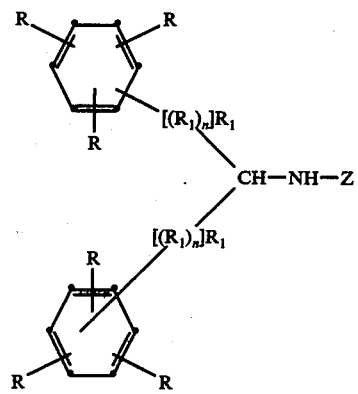

where R is hydrogen or loweralkyl;
each $n$ is alike or different and is the integer 0 or 1;
each $R_1$ is alike or different and is $C_1$ to $C_4$ alkylene;
and Z is

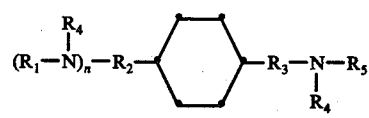

where
$R_2$ is 2-hydroxy-1,3-trimethylene, or $R_1$ as previously defined;
$R_3$ is 2-hydroxy-1,3-trimethylene, or $R_1$ as previously defined;

R$_4$ is hydrogen, aminoethyl, aminopropyl, C$_1$ to C$_4$ hydroxyalkyl, aminohydroxy C$_2$ to C$_4$ alkyl, or C$_2$ to C$_4$ dihydroxyalkyl;

R$_5$ is hydrogen, C$_1$ to C$_4$ hydroxyalkyl or C$_2$ to C$_4$ dihydroxyalkyl, aminohydroxy C$_2$ to C$_4$ alkyl, and n is as previously defined.

2. A compound according to claim 1 where $n$ is

3. A compound according to claim 2 where R$_1$ is methylene.

4. A compound according to claim 2 where R$_1$ is ethylene.

5. A compound according to claim 2 where R$_1$ is trimethylene.

6. A compound according to claim 1 where where A is 4-isopropylphenyl.

7. A compound according to claim 1 where each A is 4-t-butylphenyl.

8. A compound according to claim 1 where each A is 2-methyl-5-t-butylphenyl.

9. A compound according to claim 1 where each A is 2,4,6-trimethylphenyl.

10. N-(3-Aminopropyl)-N'-[1,5-di-(4-isopropylphenyl)-3-pentyl]-1,4-bis-(2-aminoethyl)cyclohexane.

11. N-[1,3-di-(4-t-butylphenyl)-2-propyl]-1,4-cyclohexanebis(methylamine).

12. N-[1,7-di-(4-t-butylphenyl)-4-heptyl]-1,4-cyclohexanebis(methylamine).

13. N-(3-Aminopropyl)-N'-[1,7-di-(4-isopropylphenyl)-3-pentyl]-1,4-bis-(2-aminoethyl)cyclohexane.

14. N-(3-Aminopropyl)-N'-[1,5-di-(4-isopropylphenyl)-3-pentyl]-1,4-bis-(2-aminoethyl)cyclohexane.

* * * * *